United States Patent [19]

Levy et al.

[11] 4,347,001

[45] Aug. 31, 1982

[54] AUTOMATIC PHOTOMASK INSPECTION SYSTEM AND APPARATUS

[75] Inventors: Kenneth Levy, Saratoga; Paul Sandland, San Jose, both of Calif.

[73] Assignee: KLA Instruments Corporation, Santa Clara, Calif.

[21] Appl. No.: 26,784

[22] Filed: Apr. 3, 1979

Related U.S. Application Data

[63] Continuation-in-part of Ser. No. 892,972, Apr. 4, 1978, Pat. No. 4,247,203.

[51] Int. Cl.³ ............................................. G01B 11/14
[52] U.S. Cl. ..................................... 356/398; 356/390
[58] Field of Search ................. 356/71, 138, 123, 388, 356/394, 390, 398, 399, 400

[56] References Cited

U.S. PATENT DOCUMENTS

| | | | |
|---|---|---|---|
| 3,627,918 | 12/1971 | Redpath | 356/394 |
| 3,672,778 | 6/1972 | Kern | 356/138 |
| 3,944,369 | 3/1976 | Cuthbert et al. | 356/394 |
| 4,006,296 | 2/1977 | Peterson | 356/394 |
| 4,052,603 | 10/1977 | Karlson | 356/400 |
| 4,247,203 | 1/1981 | Levy et al. | 356/398 |

Primary Examiner—R. A. Rosenberger
Attorney, Agent, or Firm—Claude A. S. Hamrick

[57] ABSTRACT

Optical inspection apparatus for detecting differences between two dies in a photomask and including a carriage for supporting the objects to be inspected and for simultaneously moving such objects along an inspection path, an illuminator for illuminating corresponding portions of the objects as they are moved along the inspection path, electro-optical detectors for individually inspecting the illuminated portions and for developing first and second electrical signals respectively corresponding thereto, electronic memories for storing the first and second electrical signals, a computer for scanning the memories and for electronically aligning a readout of the first signal relative to a readout of the second signal, and a comparator for comparing the electronically aligned signals and for indicating any differences therebetween.

3 Claims, 11 Drawing Figures

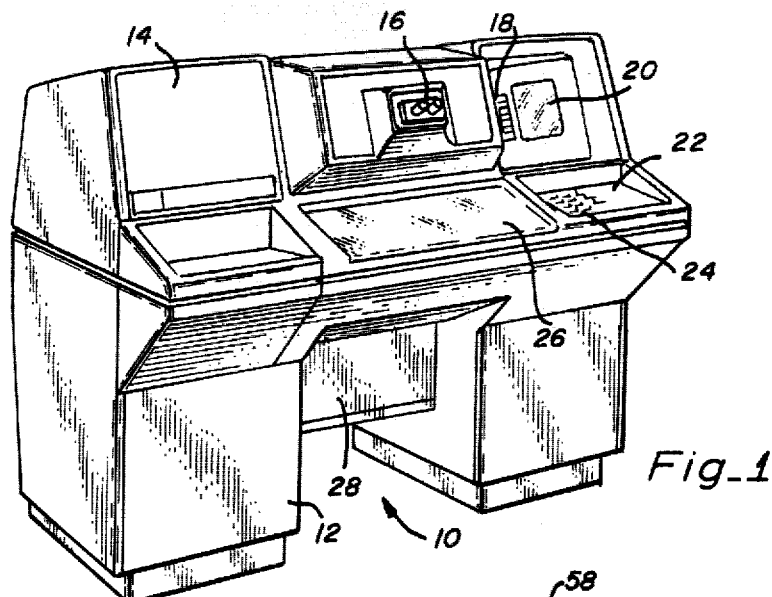
Fig_1
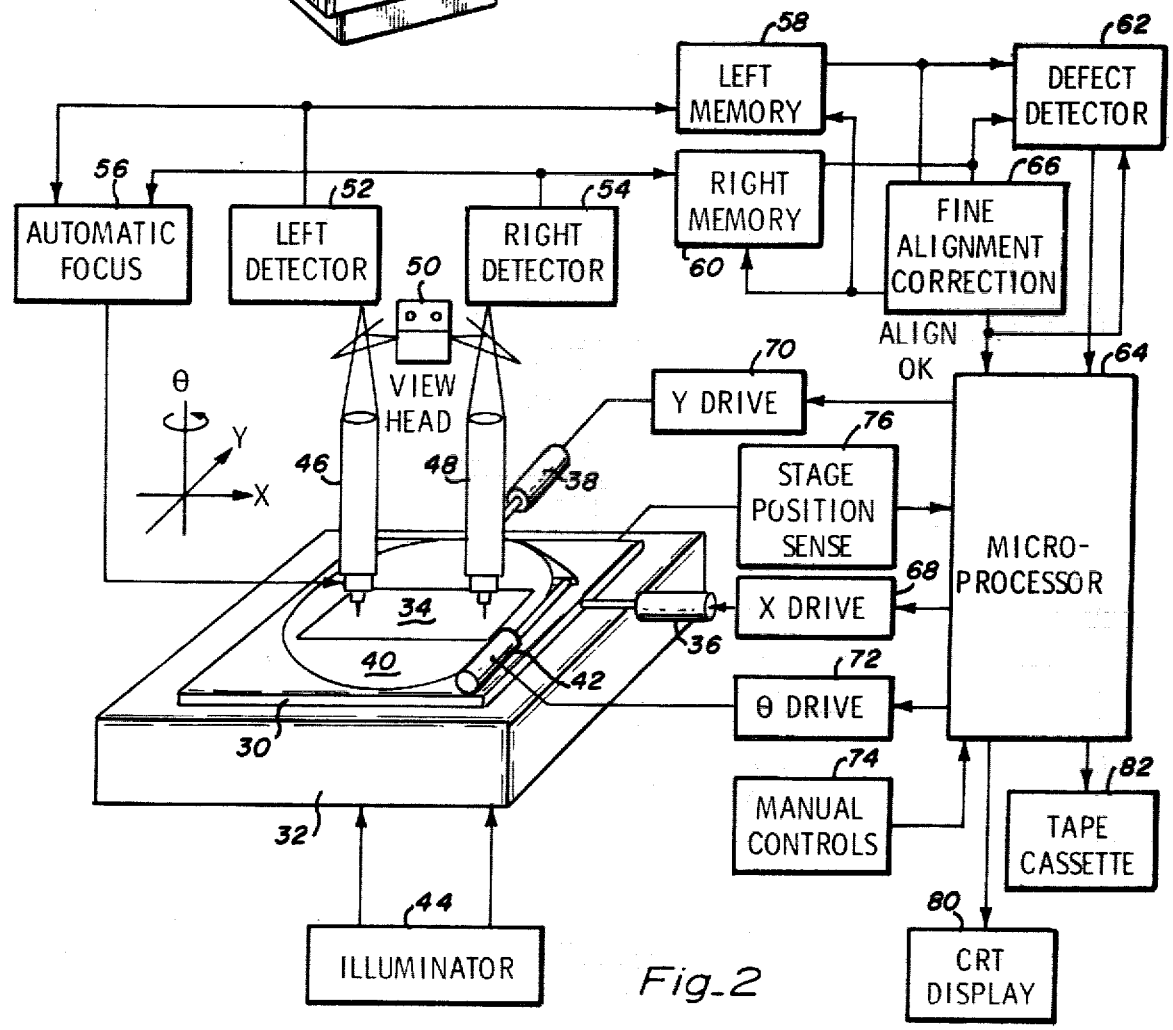
Fig_2

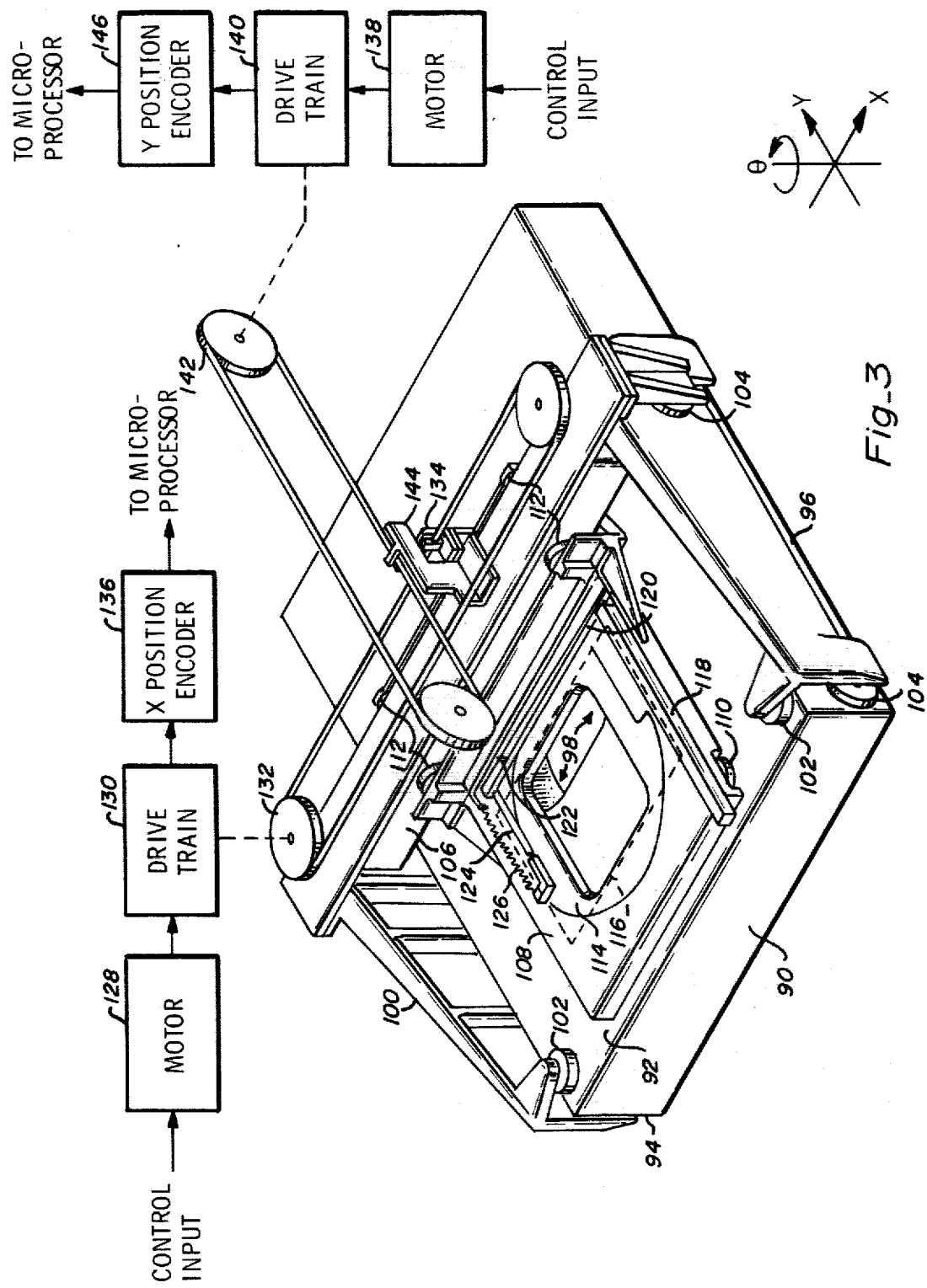
Fig_3

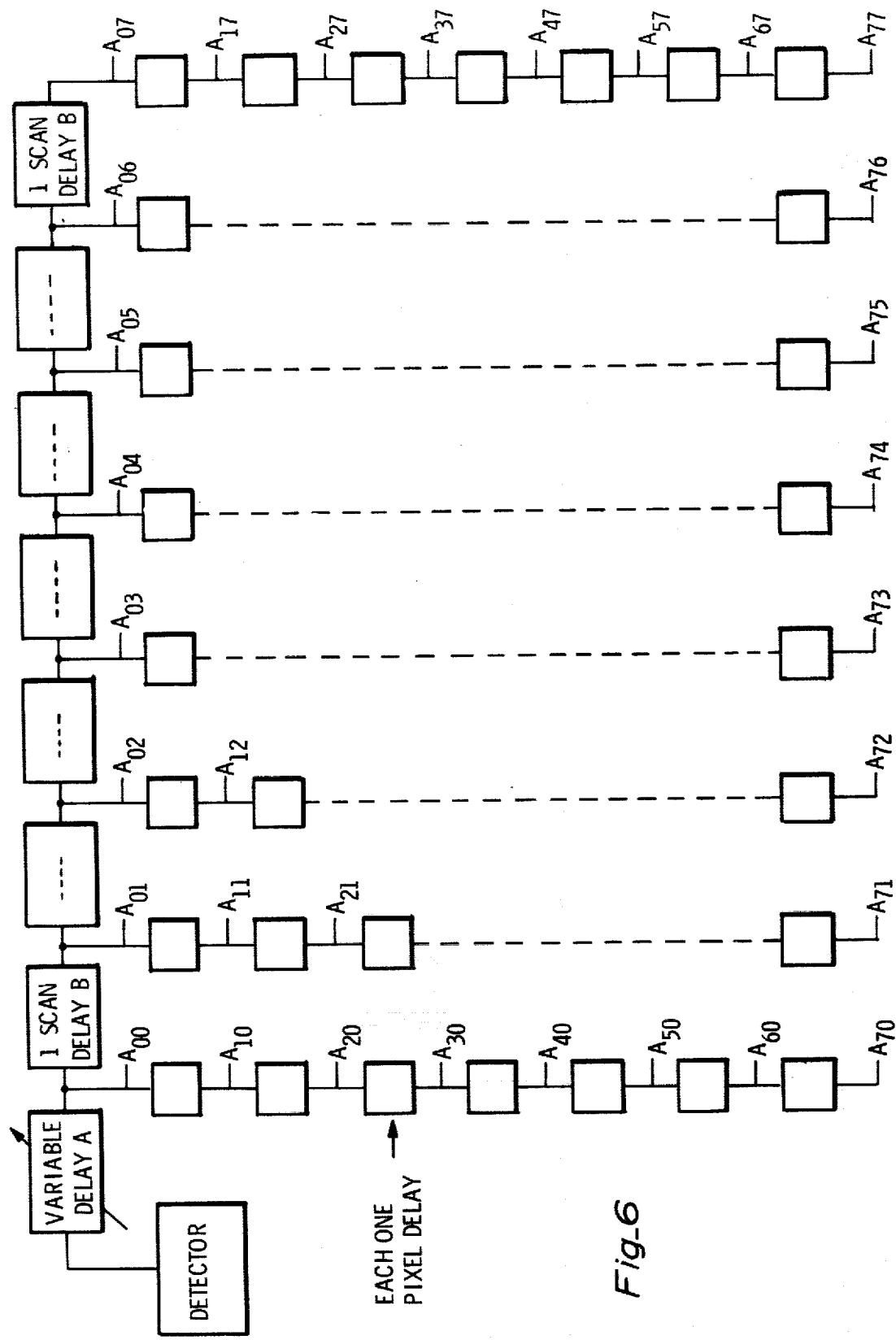
Fig_6

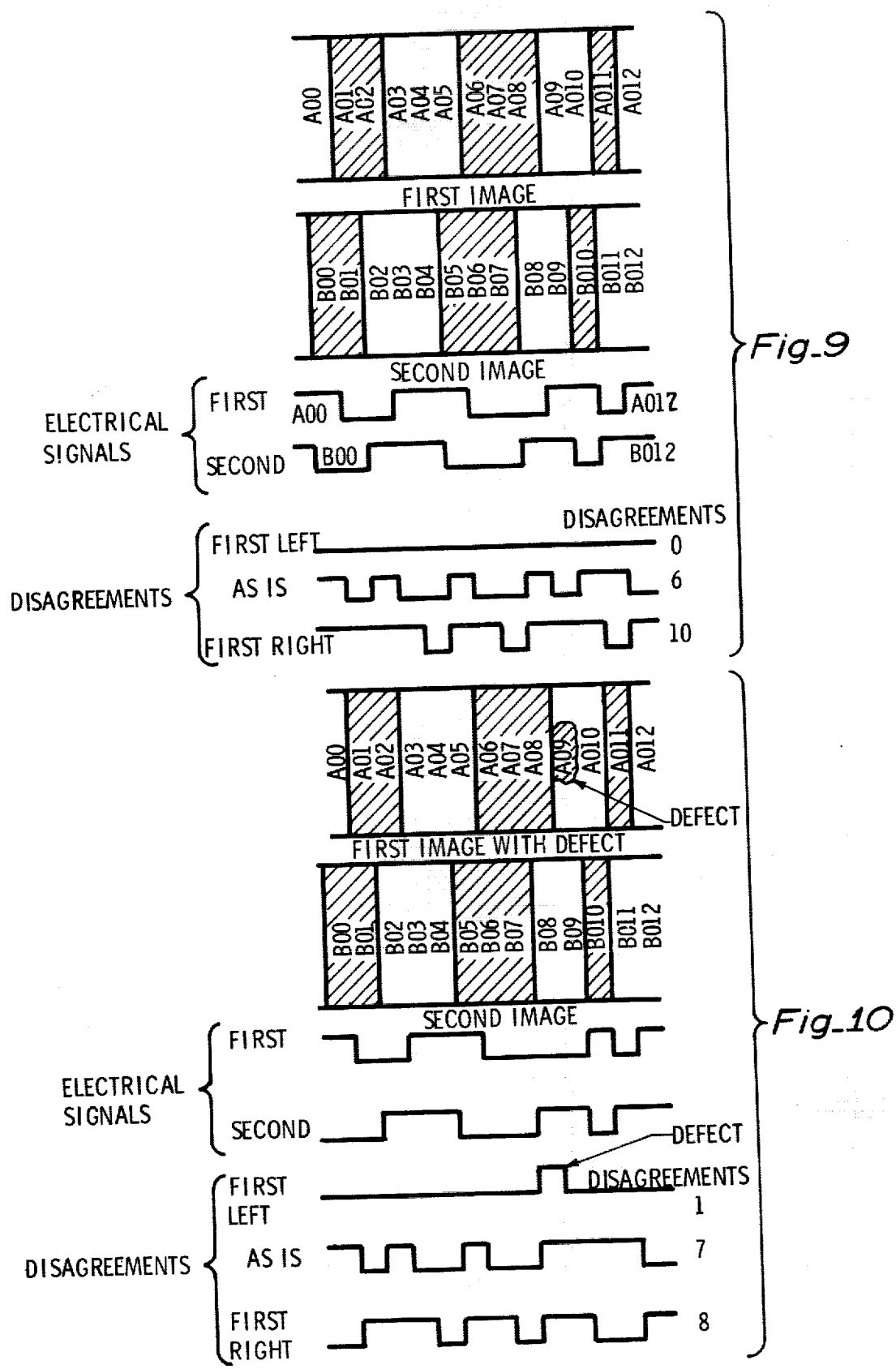

AUTOMATIC PHOTOMASK INSPECTION SYSTEM AND APPARATUS

This application is a continuation-in-part of our pending application, Ser. No. 892,972, filed Apr. 4, 1978, now U.S. Pat. No. 4,247,203, issued Jan. 27, 1981.

BACKGROUND OF THE INVENTION

1. Field of the Invention

The present invention relates generally to object inspection apparatus and more particularly to an automatic photomask inspection system and apparatus capable of locating extremely small defects in the transparencies of a photomask used to manufacture semiconductor devices.

2. Discussion of the Prior Art

One of the major sources of yield loss in the manufacture of large scale integrated circuits (LSI) is random defect in the photomasks. As chip sizes and geometry densities increase more attention must be given to mask quality in order to reduce defects to a level commensurate with acceptable yields. Accordingly, various methods of detection of photomask defects have been utilized in the past including the comparison of the subject mask to a known reference, the use of an image enhancement technique, and the use of a technique wherein adjacent die are compared to each other.

In order to determine how mask defects may be reduced it is first necessary to examine defect sources. These may be conveniently divided into three categories: (1) Defects present in the manufacture of the mask, (2) defects added to the mask during handling and storage or transportation and (3) defects added to the mask during mask-to-wafer alignment and exposure. To date a great deal of effort and capital has been expanded on category (3) defects, the industry has abandoned vacuum contact printing to reduce add on defects introduced during alignment. Handling and storage defects have been reduced by better mask carriers. Additionally, automated mask cleaners are available to remove some of the contamination added to the mask during its movements about the plant or use in an aligner.

Presently, with the industry-wide move to projection printing, increased attention is being focused on category (1) defects, those defects which are in the mask as originally manufactured. These defects have been reduced in the mask shop by placing tighter controls on the mask blanks, reducing the number of steps in the process, i.e., eliminating submaster steps, and inspecting and repairing master and submaster masks.

Mask inspection is a difficult task. For example, inspecting a 5"×5" array for 50 microinch defects means testing $10^{10}$ discrete location for conformity with the required image. A human operator takes many hours to complete such a task and is subject to fatigue. Additionally difficulty arises since defect criteria are subjective and small defects may go unnoticed. When the inspector is under pressure from volume and yield requirements, it has been shown that there may be considerable divergence between the results he obtains and an unbiased test on the same mask. Even in unbiased tests of this type many of the smaller defects may be missed. The common practice of statistical sampling to determine defect density further decreases the confidence level in the defect density measurement obtained by a human operator. If mask repair or mask matching is to be done, 100% testing is, of course, necessary as the exact location of each defect must be found.

In utilizing the first above-mentioned technique, an optical comparator is used to compare a test mask to a reference mask. The two masks are mounted on a common stage and are illuminated from below. The transmitted liquid is filtered to give complementary colors and the two images are superimposed so that common areas are black or white while differences appear as colored areas. The two masks have to be exactly aligned to each other and individually focused over the entire area to be examined. This may take considerable time and skill. Small edge misalignments cause edge coloring but a human operator can usually detect the differences between defects and edge registration. Misregistration becomes a major problem if one attempts to automate such a system. Furthermore, since the two images are widely separated in space, the mechanical requirements on the stage are stringent which inevitably results in high costs. Due to the cost alignment time and tediousness of the process, systems of this type are normally utilized as overlay comparator to check for level-to-level mask fit and line width variations rather than random defects. Extending this method to general defect detection involves processing and storage of an enormous amount of data and processing and computing speed must also be very high for reasonable inspection times to be achieved.

The image enhancement technique makes use of the fact that most valid semiconductor geometries are orthogonal whereas defective geometries are randomly oriented. To take advantage of this difference in properties between the semiconductor geometries and the defect, optical equipment is utilized which discriminates against horizontal and vertical edges by reducing their intensity relative to edges at other angles. This result can be achieved by taking advantage of the fact that when an object is illuminated by coherent light, due to diffraction the Fourier spectrum of the object is formed at the back focal plane of the imaging lens. By placing horizontal and vertical stops (spacial filters) at the back focal plane of the lens, most of the energy from the periodic horizontal and vertical structure can be blocked. This decreases the energy contribution from this structure to the final image. Nonhorizontal and vertical structures have most of the energy in other planes and are not effected as much by these spacial filters. A variation of this concept is to place spacial filters in a noncoherent illuminator of a standard microscope. If the image of the spacial filters in the illuminator lies close to the back focal plane of the imaging optics, then the system is very similar to that obtained by placing spacial filters in the imaging system. This method yields somewhat inferior results compared to the coherent illumination system but has the advantage of lower cost. These methods can be extended with some success to cover edges occurring at other common angles, i.e., 45° and 60°, and considerable visual enchancement of the defects can thus be obtained. Unfortunately, the corners of geometries contain components at every angle within their quadrant and cannot therefore be completely removed by these techniques; thus, while these methods do enable the defects to be more easily detected by the eye, they do not lend themselves easily to automatic detection.

Since masks have the unique property of repetition, all die should have the same pattern. If a difference occurs in the comparison of one die to another, comparison of either die to a third will determine which die is defective. This, of course, assumes that the defect is not repeated in the same place in the several die. There is negligible probability of this occurring unless the defect was present in the original reticle. For example, if there are 10 defects per square inch and the average defect size measures 0.001"×0.001" the probability of two random defects occurring in the same spot and thus being missed is one tenth in 100,000. At this defect size and density, only one defect would be missed every 600 masks.

The comparison between adjacent die method of inspection is most readily adaptable to fast automatic inspection. There is only one mask to set up and focus, no reference is required and because the patterns are on the same mask, the distance between them is small and fixed. This eases the mechanical tolerances of the table required to scan the mask. For production use, automatic focus is a desirable feature, particularly for inspection of large masks where the bow of the glass due to the mask weight must be considerable compared to the length of focus of the optical system.

A difficult requirement to meet even when using the comparison between adjacent die method of detection defects is optical and mechanical alignment. The precision with which the two sets of optics must be placed over the circuits and the precision with which the stage moves determines the smallest defect this type of system can detect. This can readily be seen since a misregistration of the images from the two geometries under test results in the system identifying each misregistered portion as a defect; therefore, if the mechanics of the system allow misregistration of one micron, then the system logic must reject defects smaller than one micron to avoid confusion between actual defects and misregistered valid geometry.

SUMMARY OF THE PRESENT INVENTION

It is therefore a principal object of the present invention to provide a novel, fully automatic mask inspection system utilizing the comparison between adjacent die method for defect location.

Another object of the present invention is to provide a photomask inspection system having an operational speed and precision detection capability sufficient to make 100% photomask inspection both practical and economically feasible.

Still another object of the present invention is to provide a system of the type described having optics which allow optical resolution substantially better than that of presently used projection printers.

Still another object of the present invention is to provide a system of the type described having means for automatically maintaining proper focus of the inspection optics so as to insure high resolution over the entire surface of the mask being inspected.

A further object of the present invention is to provide a system of the type described having a self-teaching mode of operation such that the operator need only perform tasks as indicated by displayed messages.

A further object of the present invention is to provide a system of the type described which utilizes microprocessor technology so as to minimize the number of controls and reduce the precision time required by the operator.

A further object of the present invention is to provide a system of the type described which automatically and electronically corrects for nonuniformity in the illumination and in the sensitivity of the sensor used to convert the light image into an electrical signal.

A further object of the present invention is to provide a system of the type described which uses an automatic correlation technique to continuously align moving images in memory thereby avoiding the necessity to hold the mechanical alignment of these images within tight tolerances.

A further object of the present invention is to process the images digitally by using algorithms which discriminate between data corresponding to defects and those corresponding to real geometries, thus reducing the volume of data to be processed.

Briefly the present invention includes precision mask carriage apparatus, illumination optics, automatic focusing optics, and electronic apparatus for comparing adjacent dies to accomplish defect location. The operation is carried out by dividing each mask into 50-microinch-by-50-microinch segments and each segment is then viewed with two objectives placed over adjacent die. As the mask moves under the objectives, the small segment of each die is digitized and stored in an electronic memory. A built-in microprocessor-based computer system completes a "best fit" digital pattern analysis between the two die, automatically eliminating the effects of mask run out, stepping errors, operator alignment and other mechanical errors. After the best fit is computed those geometries that differ between the two die are considered defective. The size and location of those defects are then stored in memory. Based upon initial operator set up information, the determination is then made as to whether the defects fall into a high density part of the circuit or in fact lie in other areas that do not effect production or yield. At the end of the inspection, information is presented showing the defects and defective dies and the stage can be automatically driven back to view each defect either on a CRT or through a binocular head. The location and nature of the defect are then recorded on magnetic tape for repair or future reference.

Among the numerous advantages of the present invention are that is provides 100% inspection of each photomask, it provides a ready history of each photomask inspected, it does not require that highly trained operators conduct tedious manual inspections and it automatically instructs the operator as to how to proceed during the inspection operation.

These and other objects of the present invention will no doubt become apparent to those skilled in the art after having read the following detailed description of the preferred embodiment which is illustrated in the several figures of the accompanying drawing.

IN THE DRAWING

FIG. 1 is a perspective view showing the console housing the present invention;

FIG. 2 is a schematic block diagram illustrating the functional components of the present invention;

FIG. 3 is a hybrid block and perspective diagram illustrating a carriage assembly in accordance with the present invention;

FIG. 6 is a block diagram illustrating a memory matrix in accordance with the present invention; and FIGS. 7-10 are diagrams used to illustrate operation of the present invention.

DETAILED DESCRIPTION OF THE PREFERRED EMBODIMENT

Figure 4:
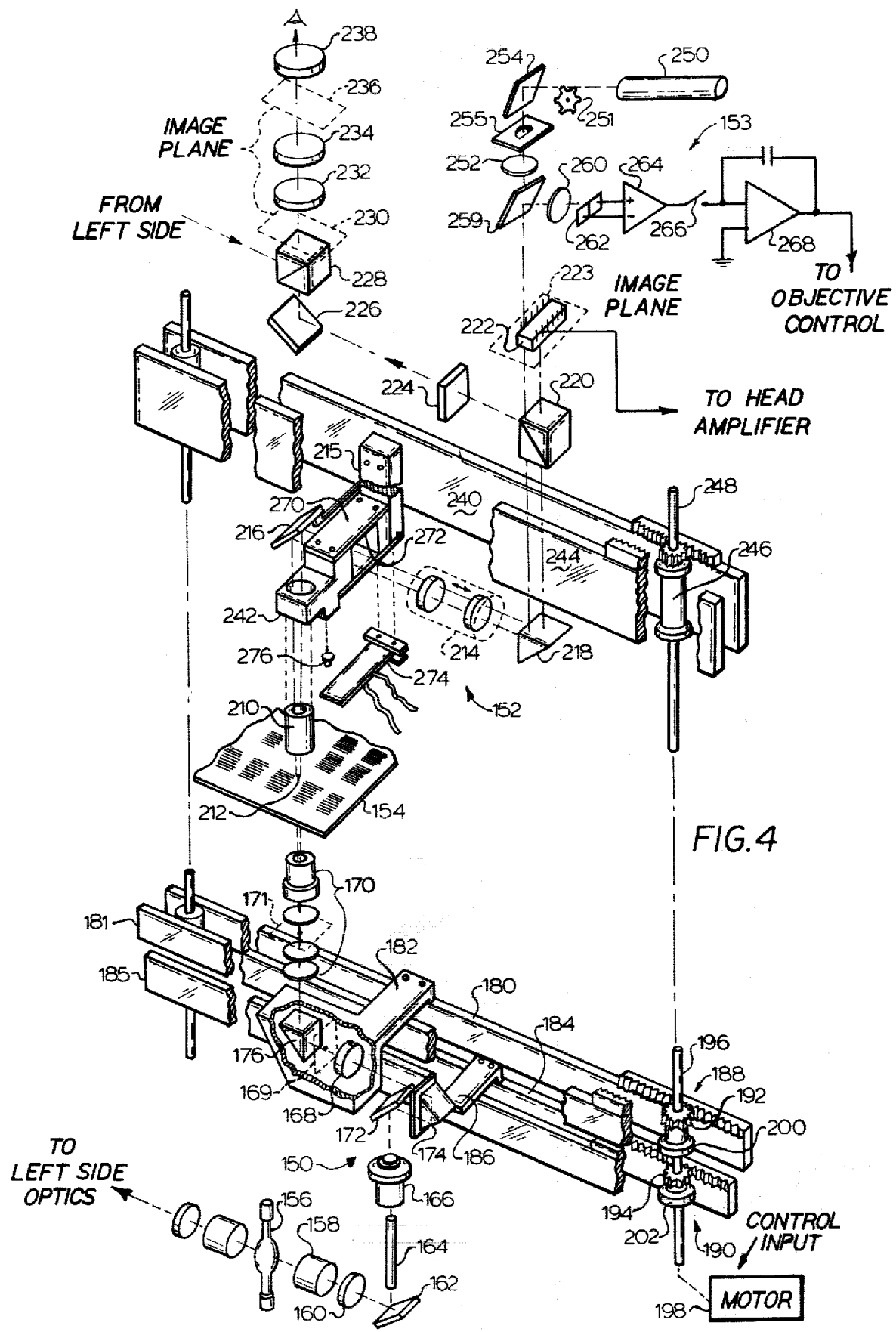
FIG. 4 is an exploded broken perspective view illustrating various components of an electro-optical system in accordance with the present invention.

Referring now to FIG. 1 of the drawing, the preferred embodiment of the console for housing the present invention is illustrated at 10. In addition to the various processing electronics this systems includes power supplies stored at 12, a roll-out card cage for easy maintenance stored at 14, a binocular head configuration microscope 16, operator controls 18 which are programmed by the systems microprocessor, a cathode ray tube display 20 for displaying operator messages and allowing mask viewing, a magnetic tape recorder 22, and keyboard stage and microscope control 24. Positioned in and about a mask loading compartment 26 is an air-bearing scanning stage mounted on a granite base and automatic focusing optical inspection objectives. An illumination system is disposed at 28 beneath the loading compartment 26.

In FIG. 2 of the drawing, the various functional components of the system are schematically illustrated and include an air-bearing stage 30 mounted on a granite table 32 for transporting a mask 34 to be inspected. The stage 30 is movable in the X and Y direction by motors schematically illustrated at 36 and 38, respectively, and the mask holder portion 40 of the air-bearing stage 30 is rotatable in the θ by a motor 42. Disposed beneath the granite table 32 is an illuminator system 44 which illuminates the bottom of mask 34 through an opening in table 32 and which will be described in more detail below. Left- and right-hand inspection optics are illustrated at 46 and 48, respectively, and cast images of the inspected die onto a binocular view head 50, and left and right detectors 52 and 54. The optical systems 46 and 48 are automatically focused by a means illustrated at 56 as will be further described below. The data output from the detectors 52 and 54 are stored in left and right memories 58 and 60, respectively, and the data stored in the respective memories are compared to each other by a defect detector 62 to provide defect detection signals which are input to the microprocessor 64. In order to electronically provide fine alignment of the two die images, a fine alignment correction system 66 which will be further explained below is also utilized. Movement of the air-bearing stage 30 is controlled by the microprocessor 64 which energizes X, Y and θ drive systems 68, 70 and 72, respectively, in response to program instruction, manual inputs from the manual controls 74 and data received from the stage position since means 76. Operator instructions and visual display of the inspected die may be alternatively displayed on a CRT display unit 80. Defect data is stored on a magnetic tape cassette recorder as illustrated at 82.

Referring now to FIG. 3 of the drawing, the operative mechanisms forming the air-bearing stage assembly is illustrated and includes a granite table 90 which has a top surface 92 which is extremely smooth and flat and two side surfaces 94 and 96 which are flat and substantially parallel to each other. The base also has a hole 98 provided in a central portion thereof through which a mask may be illuminated. A carriage 100 rides across the top 92 on a front and rear pair (not shown) of air bearings 102 and is constrained to move parallel to a surface 96 by air-bearings 104 on the right side and a similar pair of air-bearings (not shown) on the left side whereas the right side bearings are rigidly affixed to the carriage 100, the left side bearings are spring loaded against the table edge 94 so as to provide a biasing force on the carriage to insure that in moving, it is guided by the plane of surface 96 which lies parallel to and defines the wide axis. The carriage 100 also includes a cross piece 106 having smooth parallel front and rear sides which extend orthogonally relative to the table surface 96 and therefore lie parallel to and define an X axis. The mask-carrying stage 108 rides across the table top 92 on four corner positioned air-bearings 110, only one of which is shown, and is constrained to move parallel to one of the faces of cross piece 106 by front and rear air-bearings 112. Rotatably mounted to the stage 108 is an aperture plate 114 which supports a mask to be tested, the mask position is illustrated by the dashed lines 116. Rotation of the plate 114 in the counter-clockwise direction is achieved by energizing a motor located at 118 which, through a lever 120 pivoted at 122, actuates a push rod 124, the distal end of which engages one side of plate 114. A return spring 126 causes clockwise rotation when the drive of motor 118 is reversed. Movement of the stage 108 in the X direction is accomplished by means of a motor 128 which through a speed-reducing drive train 130 drives a belt-and-pulley mechanism 132, the belt of which is coupled to stage 108 by a bracket 134. Location of the stage 108 in the X direction is monitored by an X position encoder 136 which is coupled to drive train 130 and which generates an output that is coupled into the system microprocessor. Stage 108 is driven in the Y direction by means of a motor 138 which through a speed-reducing drive train 140 and belt-and-pulley mechanism 142, and associated bracket 144 is operatively coupled to the carriage 100. The position of the stage 108 along the Y axis is monitored by a Y position encoder 146 that is coupled to drive train 140 and generates a position signal for input to the system microprocessor. Although not shown in the drawing, means for monitoring the θ position of plate 114 and coupling such information to the microprocessor is also provided.

Since the stage rides entirely on air-bearings, sticking friction is absent and very small movements are possible. The table is also simpler to construct and manufacture than is a conventional machined table with rolling bearings where tight tolerances are required.

As pointed out above, the automatic inspection of photomasks requires the comparison of two supposedly identical dies on the photomask. If the two dies are exactly identical then it is assumed that both are perfect. When the two dies differ from each other at least one of them must contain a random defect. To electrically compare the two dies requires a system which can simultaneously image both dies onto two separate detectors so that the imagery can be converted to electronic signals which can then be compared by a special purpose image analizing computer. The principal requirements of the optical system are (1) means must be provided for magnifying and imaging the geometries of the dies on two diode arrays (the geometries of each separate die is imaged on a separate diode array); (2) the spacing between the two optical systems which view the two separate positions on the mask being simultaneously inspected must be variable because the spacing between the two optical systems must be an integral multiple of the spacing between the dies on the mask so that two identical positions on two identical dies may be viewed; (3) means must be provided which enable an operator to view the imagery that is being cast upon the two diode arrays so that the proper microscope spacing can be set up and the mask can be positioned properly; and (4) means must be provided for keeping the mask in the best possible focus at all times.

Each of the two areas that are to be viewed by the two objectives of the microscope must be illuminated by an illumination system. Since the inter-objective spacing of the microscope can vary the two spots of light that illuminate the mask must also vary in separation and track the movement of the microscope objectives. In addition, since the optical information is converted to electronic information, the intensity of the mask illumination is very important because the speed at which the information can be digitized from the mask is directly proportional to the illuminating intensity. Another requirement of the illuminating system is that the areas being viewed by the microscope objective system be illuminated in a very uniform manner. This is necessary so as not to confuse geometries on the mask with variations in illumination intensity.

Referring now to FIG. 4 of the drawing, an illumination system 150 and image detection and autofocus system 152 are illustrated. For purposes of simplicity, only the right side components are illustrated since the leftside components are a mirror image of the illustrated systems. Except for those components indicated as being movable, all optical system elements are mounted so as to remain stationary relative to the apparatus chassis, and for purposes of illustration, a photomask is partially depicted at 154.

The primary light source of the illumination system is a short arc mercury lamp 156 which is the brightest light source available with the possible exception of some type of laser device. Since the light radiated from a short arc lamp is equal in opposite directions and since the left and right optical systems are identical, a single lamp 156 is used for both systems. The use of a single lamp is also advantageous in that it only requires one power supply. It is further advantageous that as the lamp decreases in intensity during its life time, both illumination paths will track each other in intensity. Rays emitted from lamp 156 are collected by a collimating lens system 158 and transmitted to a lens 160 with the assistance of a mirror 162 which refocuses the lamps arc onto the end of a clad rod 164.

Since the rays impinging on lens 160 are collimated there is a one-to-one correspondence in motion of the image of the arc on the end of rod 164 with the lenses X-Y position. Therefore, by adjusting the lenses position in X and Y, the image of the arc of lamp 156 can be centered on the clad rod 164. The ability to move that image precisely is important. If a portion of the arc misses the clad rod, those rays will be lost to the system and the mispositioning will result in a lower intensity of light on the mask. Of course the arcs position can be altered by moving either the lens 160 or the lamp 156. If the lamp is moved it will also affect the corresponding arc position in the leftside optics and may affect the brightness of the illumination of the leftside image in an adverse manner.

The clad rod 164 serves two purposes, namely, it transmits the light from one position to another with virtually no loss and it helps make the illumination of the spot more uniform since the multiple reflection in the rod cause a scrambling of the light energy. If rod 164 is a square or rectangle in shape rather than the convention cylinder, the light is made even more uniform by the multiple reflections.

The light exiting from clad rod 164 is reimaged by a lens 166 onto a lens 168 which is the position of the focal plane of a focusing lens 170 and thus serves as a field lens for the lens 170 which images the light available at lens 168 onto the mask 154. It will also be noted that light passing from lens 166 to lens 168 is redirected by a mirror 172 and prism 174 the purpose of which will be explained below.

Since the focal plane at lens 168 contains the image at the upper end of clad rod 164 and that image contains virtually all of the light energy that was impinged onto the input end of the rod, i.e., the full image of the mercury arc lamp, then the light spot cast upon mask 154 is nearly as bright as the average mecury lamp arc brightness. Thus, the system is a critical illumination system with a mercury arc lamp used as the source of the critical illumination.

As previously stated, the distance between the left and right illuminated spots on the mask 154 must vary as the interobjective spacing of the microscope is varied. This is accomplished without any change in optical performance by permitting lens 168, mirror prism 176 and lenses 170 to move as a unit a distance X while prism 174 moves a distance of X/2. When such relative motion occurs, the path linked between lens 166 and lens 168 remains constant and thus relative movement of the light spot is accomplished without any change in optical performance of the system. The mechanism by which the lens assembly can be moved is illustrated to include an upper rod 180 to which the lens 168, mirror prism 176 and lenses 170 are affixed by means of a suitable mounting bracket 182 and a lower rod 184 to which the prism 174 is affixed by means of a suitable mounting bracket 186. The bars 180 and 184 are coupled to each other by means of rack-and-pinion assemblies 188 and 189 of which the circumference of the pinion 192 is twice that of the circumference of the pinion 194. Accordingly, for each increment of angular rotation of shaft 196, prism 174 will be moved one-half the distance and in the same direction as is the assembly including lens 168. Therefore, the length of the optical path between lens 166 and 168 will remain constant.

Note that a second set of bars 181 and 185 are also provided for carrying the corresponding optical components (not shown) of the leftside illuminating system and such bars are also coupled to the drive shaft 196 so as to move equal distances and in opposite directions relative to the rightside component. Thus, by using a suitable motor 198 to drive the shaft 196, any desired separation between left and rightside illuminators can be achieved with a single control input. It should perhaps be noted also that in order to insure a smooth drive motion between shaft 196 and the several rods, rollers 200 and 202 are utilized as the primary drive means while the rack-and-pinion assemblies insure positive registration.

As the mask height varies, and as will be described in more detail below, the automatic focus system varies the height of the objective lenses 210 relative to the mask 154 to keep the image on the mask in sharp focus. Objects at corresponding image planes 169 and 171 in the illumination system 150 will also focus on the sensor giving false indication of defects. The illuminator can be designed to ensure that these image planes occur away from surfaces of the lens elements, thus avoiding false indications of defects at particular objective heights corresponding to focusing on the surfaces of elements in the illuminator. This is accomplished by utilizing a number of lens elements in the lens system 170 so that the image planes which might otherwise reside on the surfaces of lens 168 or prism 176 in the system previously described will exist in the air spaces separating these optical elements.

At the top of FIG. 4, the rightside components of the microscope and automatic focusing system and their interrelationships are illustrated generally at 152 and 153, respectively. The lens 210 is an infinity corrected objective and is positioned directly above mask 154 such that the object 212 is located at its exact focal point. Light from the object 212 is collimated by lens 210 and directed into a vari-focal lens assembly (zoom) 214. The lens 210 and zoom assembly 214 thus form an equivalent single lens of magnification M. Light from the object 212 passes through objective 210, is then bent at 90° by a mirror 216 carried by a bracket 215 and passes through zoom assembly 214 where it is reimaged at the back focal length thereof. The magnification of the lens combination is $F2 \div F1$ where F2 is the focal length of lens 210.

Diverging for a moment, it should be remembered that the purpose of the subject apparatus is to compare two identical left and right objects. It is thus important that the magnification of the left and right optical systems be identical. However, it is very difficult to fabricate lenses to the focal length tolerances that are required; therefore, zoom assemblies are utilized which have variable focal lengths that can be adjusted to remove the effects of differences in the focal lengths of the respective objective lens. By varying the focal length of these lens combinations, it is possible to make the magnification of the left and right systems identical.

Another feature of the particular arrangement illustrated is that since the light passing from lens 210 to assembly 214 is collimated, a variation in the separation therebetween does not change the effective optical length of the system.

Returning now to the original discussion, light coming from object 212 passes through lens 210 where it is collimated and the collimated light is bent at right angles by mirror 216 and passed into the zoom assembly 214. Lens system 214 then converges the parallel incoming beam and images the light at its back focal length F2. Prism 218 bends the light at right angles and causes it to pass through a beam-splitting cube 220 which is fabricated such that 90% of the light passes straight through it so that a magnified image of the object 212 is formed at an image plane in which a sensor in the form of a detector diode array 222 is positioned. The diode array 222 is comprised of a string of 512 light-sensitive diodes which in effect define a scan line (see FIG. 8) and the optical imagery falling on them into electrical signals. The light that is reflected by beam splitter cube is passed through a filter 224 which is of a color complementary to that of a like filter in the leftside optical system, and impinges on a mirror 226 which then redirects it towards a beam splitter cube 228. Fifty percent of the light passes through cube 228 and is imaged on an image plane 230. Similarly, 50% of the incoming light from the leftside object is also imaged on the image plane 230. Thus, the image plane 230 contains an image of both left and right objects superimposed upon one another. Lens 232 is a field lens and redirects the diverging light at image plane 230 into a lens 234 which magnifies and reimages the left and right objects onto another image plane 236. An eye piece 238 allows an observer to view the superimposed images of the left and right objects.

For the same reasons mentioned above with respect to the illumination systems it is desirable that the interobjective spacing of the left and right optical system be variable so that each objective views a corresponding portion of a die image. Since the light passing between the objective 210 and the zoom system 214 is collimated, the separating distance can be varied without affecting the operation of the optical system. Accordingly, by mounting the objective 210 to a bar 240 by means of a suitable bracket assembly 242 and by similarly mounting the leftside objective to a bar 244 which is coupled to bar 240 by a roller and rack-and-pinion assembly 246, the spacing between the objectives can be varied by merely rotating the roller shaft 248, and by coupling the shaft 248 to the shaft 196 of the illuminator, it will be appreciated that the respective illuminating and light-detecting optics can be made to accurately track each other.

Note that since mirror 216 is affixed to bracket part 215, it will remain centered relative to the optical axis of assembly 216, even though it is moved left or right by bar 240. This feature permits relative movement between lens 210 and assembly 214.

As described above, automatic photomask inspection requires both accurate magnification and high resolution. High resolution is necessary if the system is to detect the presence or absence of small geometries on the mask. Requirements for high resolution necessitates that the optical system has a high numerical aperture since the limiting resolution of the optical system is proportional to the numerical aperture. Unfortunately, the depth of focus of the optical system is inversely proportional to the square of the numerical aperture. Thus, the more detailed one wishes to resolve on the mask, the more difficult it becomes to keep the mask in focus. However, in accordance with the present invention Applicants have provided an automatic focusing system which will now be described. The focusing system relies upon the fact that the magnification of an object through a lens system is a function of the distance an object is from the principal plane of the lens system. More specifically, the system relies upon the fact that as an image moves farther away from the lens and its ideal focus position, a point in the periphery of the field in the image plane moves in toward the optical axis and similarly as the object gets closer to the lens a point in the periphery of the field moves outward and away from optical axis. Thus, by focusing a narrow beam of light on a point in the periphery of a field and then detecting the position of this point relative to a known position, one can determine the spacing between the objective and the object. This is accomplished in the preferred embodiment by utilizing a laser 250 to provide a beam of collimated light, a spinning chopper disk 251 to modulate the light, a D-shaped, beam-defining aperture 255, and a lens 252 to focus the laser beam at a focal plane 223. Either lens 252 or the deflecting mirror 254 is positioned such that it causes the laser beam to come to a focus in plane 223' at a position in the periphery of the field of lens 214. The light focusing to a point in plane 223 diverges from that point and after being reflected by a mirror 256 passes straight through beam splitter 218 and into zoom lens 214. The light reflected from splitter 218 is lost to the system and is therefore ignored. Since the light emanates from a point in focal plane 223 which is the back focal point of zoom lens 214, it is collimated thereby and then passes through the microscope objective 210. Since the light coming into the back end of objective 210 is collimated, it will be focused to a focal point at the front focal plane of the lens. If a mirror or other specular reflector (a photomask is a specular reflector) resides at the focal plane of lens 210, then the light will be reflected back up through lens 210 as if it had emanated from an object in the object plane. The light will travel back up through lens 210 and be collimated thereby and then pass through lens system 214 and come to a focus at exactly the emanating point in the focal plane. However, in its travel back to the focal plane 223, it passes through the prism 218 and is reflected upwardly through splitter 220 to come to a focus at image plane 223.

By arranging a beam splitter 259, a focusing lens 260 and a pair of photodiodes 262 such that the lens 260 images plane 223 onto the diodes 262, and such that the specular reflector (object 154) resides in the object plane of lens 210, equal amounts of the laser light energy returning from the specular reflector will fall on both photodiodes. Similarly, if the object should move either up or down from the object plane of lens 210, the reflected image will move sideways across the photodiodes 262 due to change in magnification. At best focus, the image at image plane 223 (and on the diodes 262) is a small spot of light centered between the two diodes. As the mask moves away from best focus, the reflected light spot moves across the photodiodes and also defocuses. As the spot defocuses, it increases in size taking up the shape of the laser beam defined by the aperture 255. This image has a D shape on one side of focus and an inverted D on the other side of focus. The vertex of this image remains on the dividing line between the diodes so that no light falls on the wrong half of the diode as the image goes out of focus. This is particularly important when focusing on stationary vertical edges on the mask where without the straight-sided image edge severe defocusing would result. Without the aperture 255, although the center of the image on the diodes moves sideways, since it is also increasing in size, some of the light still falls on the other diode. On an edge out of focus, the energy at each point in the defocused image is proportional to the corresponding reflectivity of the mask at the point from which that light was reflected. Thus, although the center of the defocused spot may be displaced, to say the left, the energy on the right edge of the spot reflected from chrome on the mask 154 may exceed the energy from the rest of the spot reflected from glass, thus giving a signal of the wrong sense to the photodiodes. Since the photodiodes generate a current which is proportional to the light energy falling upon them, the difference between the current from the two diodes can be amplified by amplifier 268 and used to control the positioning of objectives 210 relative to the mask 154. In the preferred embodiment the output of amplifier 264 is passed through a switch 266, which demodulates the chopped light, to an amplifier 268 which integrates the amplified signal and develops a control signal which is proportional to the integral of the difference between the photodiode outputs.

Since the optical system is arranged such that the objective lens 210 and the corresponding leftside objective lens operate at their focal lengths and collect the light passing through them, the distance between the objectives and respective zoom lens systems can be varied without affecting the magnification or performance of the system. Accordingly, by mounting the objective lenses to flexure devices such as that illustrated at 242 and providing means for bending the flexures up and down in response to a control signal such as that developed by amplifier 268, then each objective lens can be held in focus for all object elevations within the range of control of the system.

In the preferred embodiment the flexure is comprised of a pair of horizontal plates 270 and 272 which couple the end blocks of bracket 242 to each other such that the optical axis of the supported objective lens remains vertical as the device is flexed. The flexing force is provided by a bender crystal 274, the base end of which is affixed to the rear end of the flexure and the force applying end of which is coupled to the front end of the bracket through an adjusting button 276. By coupling the output of amplifier 268 to bender crystal 274, the crystal will be actuated to cause the flexure to raise or lower objective lens 210 relative to the object plane. So long as the light energy passing through lens 260 falls equally on each of the photodiodes 262, the output of amplifier 268 will be equal to 0 and no change in the bender crystal voltage will occur. However, if more light energy impinges on one of the diodes than on the other, a voltage will be generated which causes the bender crystal 274 to move lens 210 away from the object plane. Similarly, if more light energy impinges on the other diode, the resulting voltage will cause the bender crystal to deflect in such a manner as to move lens 210 toward the object plane.

The automatic focus feature is necessary in the present invention because (1) the mask may not be flat and if the objective position were to remain fixed, the image of the microscope would both blur and change maginification; or (2) the scanning table which carries the mask may not transport its coplanar to the optical object plane, thereby causing the image to lose focus, or (3) temperature changes may cause mechanical lengths to vary and thereby cause the system to lose focus.

The above-described automatic focusing arrangement is particularly effective because it uses a laser to form the focusing beam and thus develops a spot of unusual brightness compared to the output which can be easily detected. Also, the specular coherency of the laser light makes selective filtering easily accomplished. By using lenses which are operated at their infinity conjugates, only the objective need be moved with respect to the mask. This enables the relatively weak bender crystal to focus the system. If a more conventional microscope system were to be used, the entire optical system would have to be moved together. This would require a great deal of energy on the part of the focusing mechanism. The combination of the infinity objective, the flexure mount which permits vertical motion and the bender crystal makes possible an accurate, light and inexpensive mechanism.

Figure 5A:
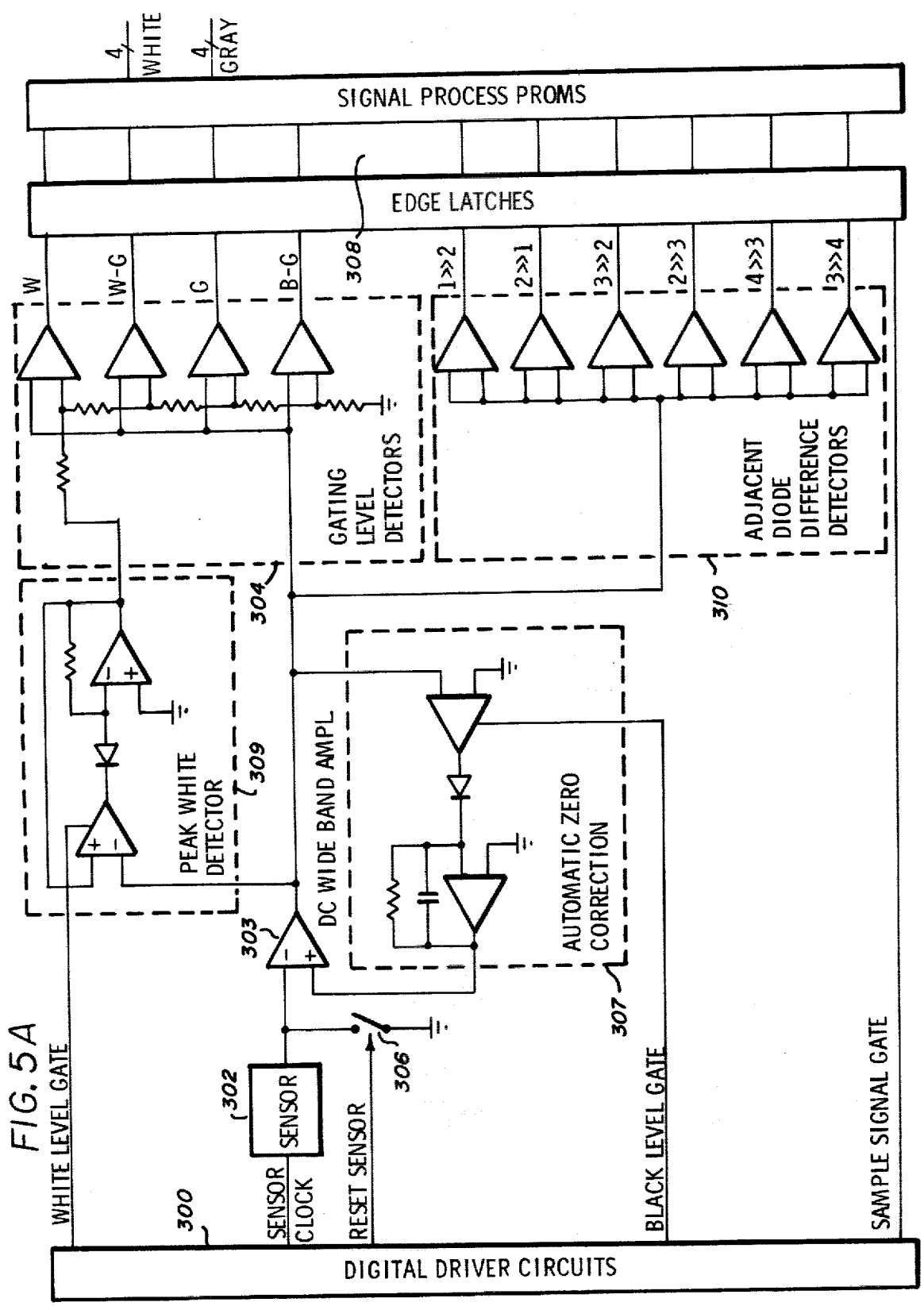
FIGS. 5A and 5B are block diagrams of detector circuits in accordance with the present invention.

Turning now to FIG. 5A, there is shown a block diagram schematically illustrating the head amplifier which is used in each detector to convert the output of the respective diode arrays 222 (FIG. 4) into useful electrical signals. Digital drive circuits 300 produce drive signals for input to the 512 element sensor 302 (diode array 222 shown in FIG. 4). The outputs from the sensor are taken via four wide band DC amplifiers 303 and are input to gating level detectors 304 which detect the light level as one of four discrete levels, e.g., white, white-grey, grey and black-grey. Black is defined as the absence of any of the above four signals at the output of the level detectors.

One purpose of the machine is to be able to process light data at high speeds. This means that the amount of energy falling on each diode is relatively small even though the light intensity is high. As each diode of the array is addressed, time is allowed for the switching transients to decay to a negligible level and then the signal from that diode is sampled and held, and the diode is then recharged by actuation of the reset sensor switch 306. The sensor is then switched to the reset sensor switch 306. The sensor is then switched to the next diode in the array and the process is repeated. Sampling is done after the amplification and level detection so that there are no errors due to the sample signal even though the signal level from the sensor is very small.

In addition, the light level varies across the field, and if one were to simply detect the absolute level on every diode, it would be difficult to detect small defects. By testing the differences between adjacent diodes, it is possible to detect very small defects, even though there may be considerable differences in the illumination across the entire field as the latter changes only slowly across the field whereas the light level from an image on the mask changes rapidly with position.

The output signals from the amplifiers are processed to produce one of three levels: black, grey or white. In the case where the signals from thelevel detectors indicate white or black level, these will pass through the signal processor 308 unchanged unless the adjacent diode difference detector 310 detects significant differences between three adjacent whites or three adjacent blacks, in which case the signal from the center diode will be changed from white to grey or from black to grey.

In the case where the level detector sends a grey signal, the output from the signal processor is always grey. If the signal from the level detectors is white-grey, the output from the signal processor is grey if the output corresponding to the previous diode from the signal processor was grey, or white if the output from the previous diode was white, unless there was a significant difference detected, in which case the output is still grey.

In a similar way, if the output of the level detector is black-grey, the output from the signal processor 308 is grey if the output corresponding to the previous diode is grey and black if the output corresponding to the previous diode is black, unless again there was a significant change detected, in which case the output would be grey.

The detector has a problem with small differences in signal level between adjacent diodes even when the light level is constant. For a signal which changes slowly across the diodes from black to white these small differences will produce alternating outputs between black and grey, or grey and white because of small differences in adjacent diode sensitivity if only three levels are detected. By detecting five levels and processing them as described above, this problem is eliminated, and there will be a single change from black to grey followed by a single change from grey to white and vice versa.

The last few diodes of the sensors are masked to prevent light from reaching them. The signal from the DC amplifiers are stored during the scan of these elements and are used to correct the amplifier output to zero. This is detected by the circuit 307 and provides automatic zero correction of the amplifier outputs. The peak level of the amplifier output is also detected and stored by the detector 309 and is input to the detectors 304 which generate the white level, white-grey level, grey level and black-grey level. Thus, if the light intensity varies, this will be compensated for and the output signal from the level comparator will be a constant fraction of the peak white signal. A variation of this circuit will remove noise due to small variations between diodes.

A digital store (read only memory or random access memory) can be programmed to provide small correction voltages for each diode which are then added to the analog output from the sensor sequentially, or used to vary the black level signal to the level detectors. This will remove any constant component of noise in the sensor array. A similar correction can be made and added to the white level signal so that changes in diode sensitivities can be compensated for. If a random access memory is used, the white level correction voltage can be programmed automatically when the sensor is responding to a clear area on the mask. This has the added advantage that small variations in the illuminator intensity can also be corrected.

Mechanical tolerances and operator misalignment of a mask to be tested cause the scanned images to be slightly misaligned. This misalignment changes with the position of the mask as it is scanned and unless such misalignment can be corrected for or predicted, defects smaller than the misalignment can not be detected. In the preferred embodiment a high speed solid state memory is used to store a small portion of the images from each sensor and the delay between writing and reading is altered until the images correspond. Data is read from memory as two $8 \times 8$ matrices of points, each of which may be white, grey or black. Once alignment is established, it may be tracked by comparing a pixel near the center of one matrix with the corresponding pixel in the other matrix, with the pixel above, and also with the pixel below. If the pixel in the center agrees most often, then that is the best alignment. If the adjacent pixel above the center agrees with the center pixel in the other matrix most often, the read addresses must be adjusted one place up on one side so that the center pixels once more agree most often. Similarly, alignment from side to side can be tracked by determining which pixel of three adjacent ones agree most often.

This scheme does not yield correct tracking data unless the alignment is close to the right place. Therefore, it is necessary to determine initial alignment by some other means.

Figure 5B:
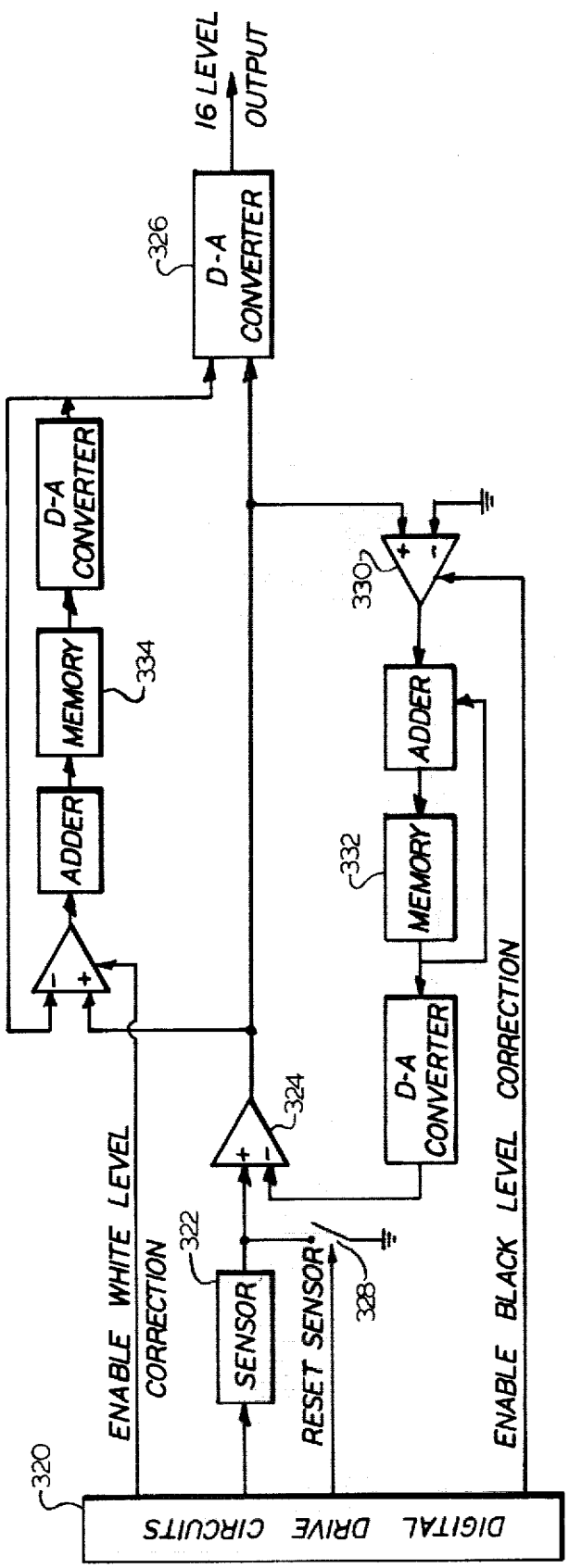

In FIG. 5B, an alternative head amplifier diagram is shown which may be used in each detector to convert the output of the respective diode arrays 222 (FIG. 4) into useful electrical signals. Digital drive circuits 320 produce drive signals for input to the 512 element sensor 322 (diode array 222 shown in FIG. 4). The outputs from the sensor are taken via four wide band DC amplifiers 324 and are input to a-d converters 326 which detect the light level as one of 16 discrete levels.

As indicated above, one purpose of the machine is to be able to process light data at high speeds. This means that the amount of energy falling on each diode is relatively small even though the light intensity is high. As each diode of the array is addressed, time is allowed for the switching transients to decay to a negligible level and then the signal from that diode is sampled and held, and the diode is then recharged by actuation of the reset sensor switch 328. The sensor is then switched to the next diode in the array and the process is repeated. Sampling is done after amplification and level detection so that there are no errors due to the sample signal even though the signal level from the sensor is very small. Before scanning, the sensor is automatically positioned over a black area so that no light falls on the sensor. Comparator 330 is used to compare the amplifier output signal to zero and adjust the digital number stored in memory 332 for each diode so that the amplifier output is zero corresponding to black. This eliminates offsets in the amplifiers and on individual diodes in the sensor.

In addition, the light level varies across the field so that defects in different locations produce different signal levels. Therefore, before scanning the mask, the microscope is moved automatically over a clear area of the glass and the signal from each diode in the array is stored in memory 334. This signal corresponds to absolute white and is used as a reference in a-d converter 326. The output signal from 326 is therefore independent on the incident illumination, the diode and amplifier sensitivity and the sensor nonuniformity and is only proportioned to the blackness of the mask at each particular point.

Mechanical tolerances and operator misalignment of a mask to be tested cause the scanned images to be slightly misaligned. This misalignment changes with the position of the mask as it is scanned and unless such misalignment can be corrected for or predicted, defects smaller than the misalignment cannot be detected. In the preferred embodiment, a high-speed, solid state memory is used to store a small portion of the images from each sensor and the delay between writing and reading is altered until the images correspond. Data is read from memory as two 8×8 matrices of points, each of which may be one of 16 levels. Once alignment is established, it may be tracked by comparing a pixel near the center of one matrix with the corresponding pixel in the other matrix, with the pixel above, and also with the pixel below. If the pixel in the center agrees most often, then that is the best alignment. If the adjacent pixel above the center agrees with the center pixel in the other matrix most often, the read addresses must be adjusted one place up on one side so that the center pixels once more agree most often. Similarly, alignment from side to side can be tracked by determining which pixel of three adjacent ones agree most often.

This scheme does not yield correct tracking data unless the alignment is close to the right place; therefore, it is necessary to determine initial alignment by some other means. It is possible to tell if alignment is good (but not in which direction to move) by simply counting the number of disagreements between the center pixels compared to the number of edges in the image. On a normal mask the defects will be very few and thus if the images are aligned, there will be few disagreements between corresponding pixels. However, misalignment will yield large numbers of disagreements between the color of the corresponding pixels at every edge.

In the preferred embodiment, initial alignment is performed by a program which steps the relative read address in a spiral pattern, starting with the addresses which correspond to perfect mechanical alignment of the images and then alternately stepping the relative address and testing for a low number of disagreements between the center pixels and a satisfied fine align; i.e., one that has more agreements between center pixels than between the center pixel and the one to the right and left, top and bottom. Once this position is found, tracking proceeds as described above.

Even with the alignment scheme described above, the images do not remain in exact and perfect alignment since some misalignment is necessary to cause an alignment correction. In some cases a portion of the mask may contain no data and when a new image appears, it is necessary to correct the alignment but not collect false defects in the mean time; thus, several algorithms are used to detect defects based on the differences between defects and valid geometries. The defect algorithms operate on a field of 8×8 pixels. This is a somewhat arbitrary size and depends on the expected variations in alignment and systematic errors. Data is moved through the defect detector one pixel at a time; thus, every pixel is at some time in the center of the 8×8 matrix.

Referring now to FIG. 6 of the drawing, there is shown a matrix of the type described above. Each memory consists of a variable delay A which can delay the signal by a given number of scan lines (X delay) and a given number of discrete pixels along a particular scan line (Y delay). This is followed by fixed delays B, each equal to one scan line.

The signals from the junctions of these delays B represent a line of pixels of fixed length (8 in the diagram) in the X direction at a given X position relative to the sensor position given by the X delay, and a given Y position along the sensor given by the Y delay. By further delaying these signals by single-pixel delays (which can constribute to delay B), lines of pixels in the Y direction are obtained. Thus, two rectangular arrays of pixels are formed which correspond to two small rectangles on the mask.

The signals received by the sensors typically come from slightly misaligned geometrics on the mask. This misalignment may be due to initial operator misalignment or misalignment occurring due to imperfections in the mechanical scanning system.

Since the mask is in motion in X direction and is scanned by the sensor in the Y direction, the difference in alignment represents a given X and Y delay between the same images impinging on the left and right sensors. By adjusting the delay between the signals from the sensors, this misalignment can be removed and the signals made to correspond to identical portions of the mask.

In principle, the memory could be implemented with shift registers; however, for maximum speed of operation, the present design uses high speed random access memory. This has an advantage in that the data can be continuously recorded and if one wishes to align the signals, he can immediately change the read address. If the design is implemented with a shift register as described previously, there will be a delay between detecting those images which are misaligned and correcting this alignment by changing the delay. The FIG. 6 diagram shows the left memory. The right memory is identical except that a fixed delay could be used in one channel with a variable delay in the other channel only.

Algorithms which are used to detect defects are the following. For defects in a clear field, the center pixel in one field must be matched by a pixel of the same color somewhere in the other field.

For defects close to a single edge: (a) if field A contains no horizontal transitions, i.e., only horizontal edges or a clear field, the direction of the vertical pixel pair transition in field B must be matched by a vertical transition of the same direction in field A. Only transitions above a certain magnitude are defect candidates unless matched by a transition in the other field. The optical-to-electrical transfer function will be slightly different for the right and left optical systems. Hence, it is possible for very small images to be missed in one side but just seen in the other. Thus, very small transitions corresponding to small image changes are only used to match and are not themselves defect candidates; (b) the above algorithm applied at right angles.

For defects joined to an edge: (a) if field A contains a vertical transition on the two adjacent center pair pixels and field B contains no vertical transitions anywhere in the same directions, this is identified as a defect; (b) this also may be applied at right angles.

Single transitions above a certain threshold even on edges must be matched by corresponding transitions in the other field or they are defects.

In operation, at the start of the operational sequence, the X-Y air-bearing stage is automatically moved into the load position. The mask to be tested is then inserted in the holder and the two images from the two illuminated die are presented to the operator as a single overlapping picture in the binocular viewhead 50 (FIG. 2) at 400X magnification. The images are of complementary colors so that when superimposed and perfectly aligned, a single black-white image is formed. Superposition is achieved easily by the use of push-buttons and servo drives for X, Y, $\theta$, and image separation. Alignment of the images in the binocular head also yields alignment of the images on the left and right image detectors 52 and 54, respectively. Only approximate manual image alignment is required since the data is electronically processed prior to defect detection as described above.

Figure 7:
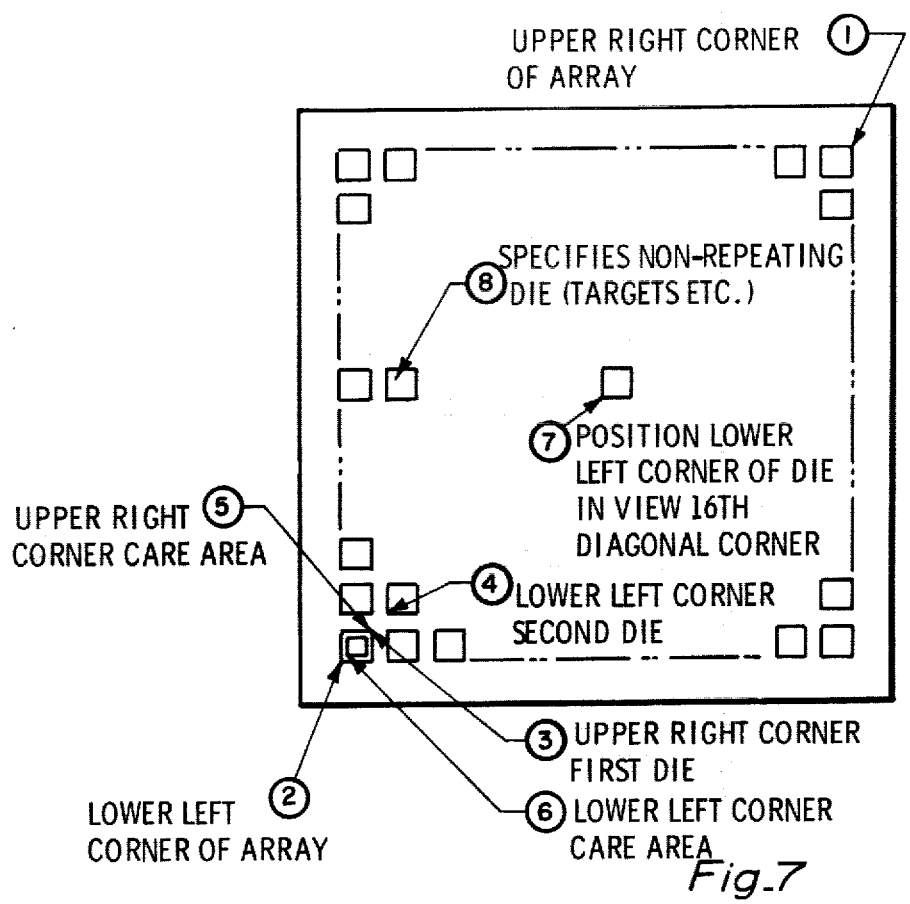

Once the images are correctly positioned, the operator then defines important mask parameters such as top lefthand and bottom righthand corner of the mark array, die size, areas of interest within the die and positions of dropouts. in FIG. 7 there is a pictorial view showing the points of the mask that the operator specifies either by positioning these points under a cross which appears in the binocular view head or by inserting a prepared magnetic tape in the tape cassette. Manual setup of a mask takes about five minutes. On round arrays the extreme left and right and top and bottom positions of the array are entered.

Figure 8:
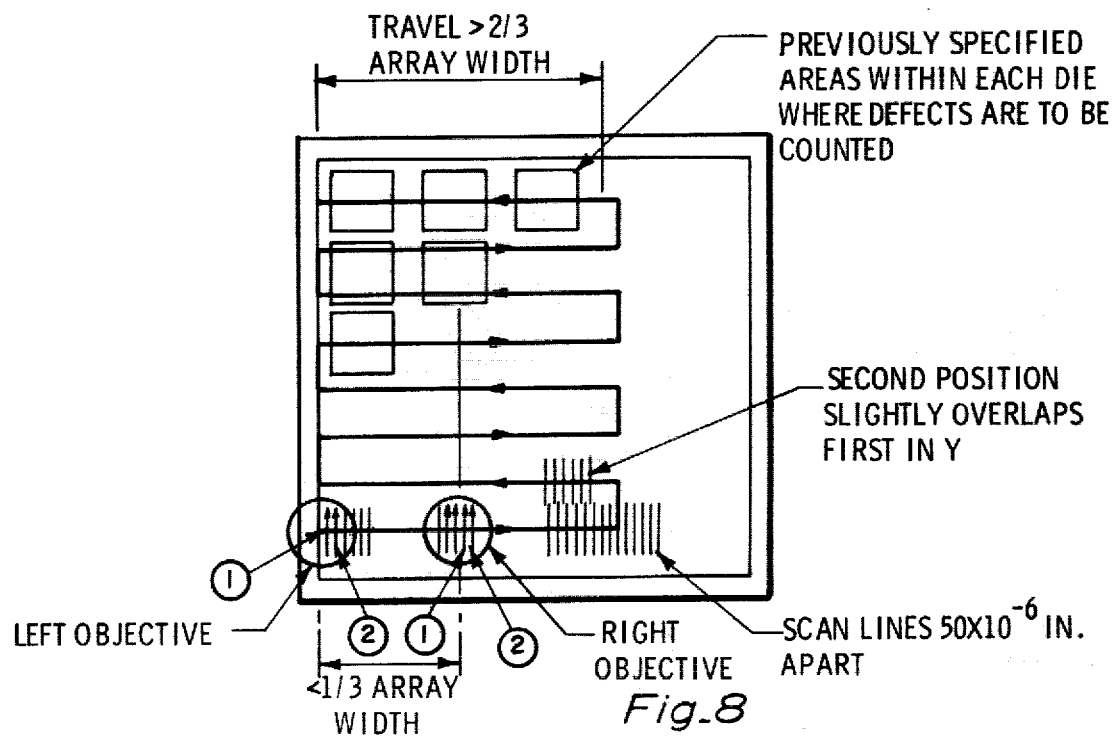

Once the data points are determined, the microprocessor 64 stores them and computes the areas of the mask to be viewed and the area on the mask in which the presence of defects can be ignored (called "don't care" regions). The stage drives are then activated and the mask is scanned automatically in a pattern as shown in FIG. 8 of the drawing. The scan rate is 2 square inches per minute. Thus, a 4"×4" array takes 8 minutes to scan. Data from the mask is converted to digital electrical data and entered into the high speed left and right memorie 58 and 60.

The continuous automatic fine align system is used to find, track and compare the images stored in memory. The mask can be thought of as being divided into discrete squared $50 \times 10^{-6}$ inches on a side. When the two images are perfectly aligned, the data from each pair of squares of pixels will agree. Automatic alignment is based on three assumptions. The first is that the pairs of pixels which do not agree due to defects are few in number compared to those which agree when the two images are perfectly aligned. The second is that the misalignment is less than the average geometry size. Therefore, misalignments of 0.5 mils. can be tolerated. The third requirement is that the rate of change of stage position, and this requirement is easily met.

With these provisions in mind, consider two simple images (representing only a small portion of the mask) consisting of vertical bars stored in memory, these are shown in FIG. 9 of the drawing. The first obvious conclusion is that such an image yields no data from which vertical alignment can be made and only horizontal alignment is possible from vertical edges. Similarly, only vertical alignment is possible from horizontal edges.

Each image is divided into a matrix of pixels. The position of these pixels in memory depends on the alignment of the images in space. High speed correlation is employed to detect defects and correct alignment. A comparison is made between the images and the position seen by the sensor and the same image electronic shifted left and right by one pixel. There is clearly better agreement in the example shown when the first image is shifted to the left. Note now what happens when defects are introduced into one field as illustrated in FIG. 10 of the drawing. The number of disagreements increases in all cases but the aligned images still produce the lowest number of disagreements. These disagreements are of course the defects. Fine alignment in the vertical direction is carried out in the same manner using horizontal edges. Alignment correction and defect detection is carried out continuously at the same rate at which new data is being collected. Thus, the memory need only be of sufficient size to accommodate the maximum misalignment. Provision is made for a misalign of +0.006 or −0.006 in the image positions which is more than adequate to compensate for table skew and initial error with the 6 inch mask.

To detect the smallest defects the optics are diffraction limited with a numerical aperture of 0.4. This is approximately twice the numerical aperture of projection aligners now on the market and therefore will resolve defects smaller than projection aligners can print. For detects $50 \times 10^{-6}$ inches, the probability of detection is about 50% rising to 95% at 100 microinches. The larger the numerical aperture, the smaller the depth of focus becomes. The depth of focus of the present system for acceptable image edge traces is 1 micron. Since the mask bow may be several microns, automatic focusing is essential when scanning the mask. The edge trace of the electronic signal from each sensor is used to automatically adjust the objective position. Initial focus is found by an incremental automatic search over a 10 mil area. Since the mask is referenced by the top (chrome) surface, the focus position is not affected by the mask thickness.

The practical importance of defects is related to their size and position on the mask. Defects lying within scribe lines, for instance, are unlikely to cause problems. This may also apply to regions repeated within each die and to similar die used for alignment targets, etc. Such areas are recalled from the microcomputers memory and defects occurring in these regions are ignored. At the end of each test, the information is presented giving the defects and defective die. The stage can then be automatically driven back to view each defect and enter on tape or other output medium, e.g., external computer, etc., the location and nature of the defect.

In addition to cataloging defects, determining their size and position, and controlling the stage, the microprocessor permits a convenient man/machine interface. Each step of the test procedure and operating instructions is displayed as a request on a computer-generated TV display 20 (see FIG. 1) beside which are four buttons 18. (Messages and languages other than English can also be written by reprogramming the appropriate PROM.) As each message appears, only those buttons which relate to performing the appropriate task are enabled. When the task is complete the button indicated must be pushed. Pushing an improper button for the appropriate task is simply ignored. For instance, the corner of the lower left die is centered in the microscope in response to the appropriate request on the TV monitor. From the X-Y stage position the computer creates a matrix of die positions across the wafer. It then automatically drives the stage to the calculated position of the corner of the 16th die in a diagonal direction and commands the operator to "center bottom left corner of die in optics". If the resulting stage position differs significantly from the calculated position, the operator is instructed to repeat the first measurement. This self-checking, self-learning system of operation reduces set-up error.

The machine has a capacity for masks between 3 and 6 inches on its side and 0.060 to 0.120 inch thickness. The compartment which encloses the mask and optics during tests is continuously purged with nitrogen providing a clean environment for the mask. After the scan is completed, the defects may be cataloged and their locations recorded on magnetic tape; this tape can be used in conjunction with the mask and subsequent operations to inspect and repair each defect.

Since the mask alignment operation of the present invention is performed electronically by altering the read address, in principle only the magnification of the optical system need be increased to detect smaller and smaller defects. Mechanical alignment errors can still be removed by the electronic alignment system.

Although the present invention has been described above in terms of a preferred embodiment specifically designed to test photomasks, it will be understood that the system or various parts thereof could be adapted for other applications. For example, by employing incident illumination instead of illumination through the object, it would be possible to inspect semiconductor wafers for defects using the same detection system. Accordingly, it is Applicants' intent that the appended claims be interpreted as covering all such alterations, modifications or other applications as fall within the true scope of the invention.

What is claimed is:

1. Optical inspection apparatus for detecting differences between two like objects, comprising:
   carriage means for supporting the objects to be inspected and for simultaneously moving such objects along an inspection path;
   illuminator means for illuminating corresponding portions of said objects as they are moved along said path;
   electro-optical means for individually inspecting said illuminated portions and for developing first and second electrical signals respectively corresponding thereto, said electro-optical means including separate optical systems for respectively collecting light from said corresponding portions of the inspected objects, and each said system including photosensitive detector means responsive to the collected light and operative to generate electrical signals commensurate therewith, each said separate optical system further including a movable member, an objective lens carried by said movable member for collimating light rays received from one of said objects, a variable focal length lens assembly for receiving the collimated light rays and focusing them onto an image plane at said detector means, an adjustable attachment means mounting said objective lens to the said movable member, focus monitoring means for determining the position of said objective lens relative to the inspected object and for developing an adjustment signal, and adjustment means responsive to said adjustment signal and operative to adjust said attachment means so as to maintain said objective in a focused position relative to the inspected object, the movable member of one of said separate optical systems being mechanically coupled to the movable member of the other of said separate optical systems such that movement of one of said members in one direction causes a like movement of the other of said members in the opposite direction, said focus monitoring means including a laser for passing a narrow beam of light through at least a portion of said separate optical system at an angle relative to the optical axis thereof and onto a peripheral spot of the inspected object, and means disposed along said optical axis for detecting the position of said spot relative to said focused position and for developing said adjustment signal commensurate therewith, said focus monitoring means further including an aperture disposed within the path of the incident laser beam so as to cause the beam spot to have a predetermined configuration which permits unambiguous detection of out-of-focus images caused by an object surface having varying reflectivity;
   memory means for storing said first and second electrical signals;
   means for scanning said memory means and for electronically aligning a readout of said first signal relative to a readout of said second signal; and
   means for comparing the electronically aligned signals and for indicating any difference therebetween.

2. Optical inspection apparatus as recited in claim 1 and further including beam-splitting means disposed along the optical axis of said system for coupling a portion of the imaged light into binocular means.

3. In an optical inspection apparatus including carriage means for transporting two like objects along an inspection path, means for illuminating corresponding portions of the objects, and electro-optical means for individually inspecting the illuminated portions, an improved electro-optical means comprising:
   first and second separate optical systems for respectively collecting light from the corresponding portions of the inspected objects, each said separate optical system including a movable member, an objective lens carried by said movable member for collimating light rays received from one of said objects, a variable focal length lens assembly for receiving the collimated light rays and focusing them onto an image plane, said movable member being mechanically coupled to the movable member of the other of said separate optical system such that movement of one of said members in one direction causes a like movement of the other of said members in the opposite direction, each said separate optical system further including an adjustable attachment means mounting said objective lens to its corresponding movable member, focus monitoring means for determining the position of said objective lens relative to the inspected object and for developing an adjustment signal, and adjustment means responsive to said adjustment signal and operative to adjust said attachment means so as to maintain said objective lens in a focused position relative to the inspected object, said focus monitoring means including a laser for passing a narrow beam of light through at least a portion of said separate optical system and onto a peripheral spot of the inspected object, and means disposed along the optical axis of said system for detecting the position of said spot relative to a predetermined focused position and for developing said adjustment signal commensurate therewith, said focus monitoring means further including an aperture disposed within the path of the incident laser beam so as to cause the beam spot to have a predetermined configuration which permits unambiguous detection of out-of-focus images caused by an object surface having varying reflectivity; and photosensitive detector means disposed at said image plane for receiving the focused light rays and operative to generate electrical signals commensurate therewith.

* * * * *